Dec. 3, 1957 | E. R. DANEGGER | Plant Pat. 1,664
LIGUSTRUM PLANT
Filed March 20, 1957
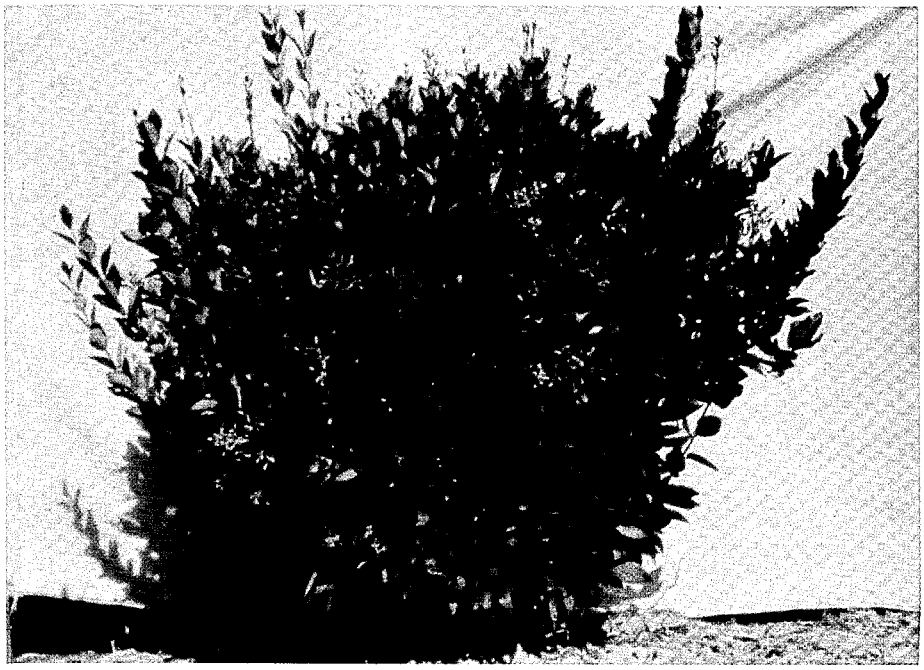
INVENTOR
Emil R. Danegger
By Orville M. Kile
PLANT PATENT AGENT United States Patent Office Plant Pat. 1,664
Patented Dec. 3, 1957

1,664

LIGUSTRUM PLANT

Emil R. Danegger, Milford, Del.

Application March 20, 1957, Serial No. 647,463
1 Claim. (Cl. 47—59)

My present discovery relates to a new and distinct variety of Ligustrum plant found among cuttings of *L. lucidum,* unpatented, taken from plants growing in our nursery at Milford, Delaware. These cuttings were rooted by me at our nursery and as they grew this particular plant—my new variety—stood out clear and distinct among the surrounding plants. Although it is not definitely known from which of the several plants of *L. lucidum* the present variety originated, it was either a bud sport or a whole-branch sport of one of them.

My attention was first drawn to the new variety because of its compact, erect growth in contrast to the semi-upright and more spreading growth of the other plants also grown from cuttings of *L. lucidum.* These features became more evident as the plant grew taller. In addition to the above-mentioned features, it was later noted that the new variety is much more hardy in severe cold, and its foliage is smaller and a much darker color throughout the winter than the foliage of the parent variety.

The year following my observance of the erect growth of this new plant, I rooted at our nursery at Milford, eight cuttings of the new variety. Since that time I have asexually reproduced, at the same location, a large number of plants from these original cuttings, and the distinguishing characteristics appear to be permanent.

Shown in the accompanying illustration is a typical specimen of this new variety in characteristic form before shearing, and in approximately its true colors at the base of the plant. The lighter appearance of some of the leaves at the upper part of the plant is due to the reflection of light.

In the following detailed description, color plate references indicate Ridgeway's Color Standards and Nomenclature. Where no reference is given, the usual dictionary meaning of the term is intended.

*The plant*

Growth: Very compact and erect shrub form rather than the spreading, semi-erect form of most Ligustrum types. Growth is heavy and compact all the way to the ground. A five-year-old bush or shrub is about 3 feet tall, although it has been sheared for cuttings in previous years. Undoubtedly an unsheared five-year-old plant would be taller.

Cold resistance: Very hardy in temperatures tested. At a temperature of about 10 degrees F. above zero, our *L. lucidum* froze back badly but this new variety, growing under similar soil, moisture and exposure conditions, stood up fine, with only a few soft tips affected.

Disease resistance: No disease of any kind has been observed on this new variety.

Stems: Sturdy and strong. Irregularly covered with tiny glands. (Bumps) Internodes are variable—from 2 to 6 inches in length, depending on the age of the particular part of the wood viewed.

Foliage:

*Quantity.*—Abundant.

*Color.*—Very dark green. The exact color does not appear in Ridgway's Color Standards and Nomenclature but is darker than Dusky Olive (Pl. XLI) and not so blue as Dull Blackish Green (Pl. XLI). The under surface is approximately Oil Green (Pl. V). Particularly noticeable is the fact that during the several years that this plant has been grown, its color has remained green throughout the winter in this area. It has not developed yellow or browned foliage in the winter as is the usual expectation with other varieties grown in this area.

*Aspect.*—Shiny on upper surface; dull on under surface.

*Texture.*—Smooth; heavy; leathery.

*Position.*—In opposite pairs. Two-ranked on twigs, growing rather upright.

*Shape.*—Elliptical, with acute to acuminate apex. Somewhat undulate.

*Size.*—Typical leaf measures 2 to 2½ inches long and 1 to 1⅛ inches wide.

Flowers: Small funnel-shaped flowers grow in terminal panicles; quantity appears smaller than on *L. lucidum,* but not sufficiently different as to constitute a novel feature.

Fruit: Usually clusters are smaller and berries larger than those of *L. lucidum.* Clusters vary greatly in similarity—no two appear alike. Berry—one-seeded; bluish-black.

Having thus disclosed my discovery, I claim:

The new and useful variety of Ligustrum plant, substantially as herein shown and described, characterized particularly as to novelty by its erect and compact growth habit (compact from ground to tip); its very dark evergreen foliage of medium size and slightly undulate form; and its resistance to severe cold.

No references cited.